(12) United States Patent
Krusor et al.

(10) Patent No.: US 11,026,578 B2
(45) Date of Patent: Jun. 8, 2021

(54) ALERTING FOR LOSS OF FULL SKIN CONTACT OF PATIENT ELECTRODES

(71) Applicant: West Affum Holdings Corp., Grand Cayman (KY)

(72) Inventors: Blaine Krusor, Seattle, WA (US); Isabelle Banville, Newcastle, WA (US); Joseph Leo Sullivan, Kirkland, WA (US); David Peter Finch, Bothell, WA (US); Daniel Ralph Piha, Bellevue, WA (US); Laura Marie Gustavson, Redmond, WA (US); Kenneth Frederick Cowan, Kirkland, WA (US); Richard C. Nova, Seattle, WA (US); Carmen Ann Chacon, Vashon, WA (US); Gregory T. Kavounas, Bellevue, WA (US)

(73) Assignee: West Affum Holdings Corp., Grand Cayman (KY)

( * ) Notice: Subject to any disclaimer, the term of this patent is extended or adjusted under 35 U.S.C. 154(b) by 128 days.

(21) Appl. No.: 16/003,531

(22) Filed: Jun. 8, 2018

(65) Prior Publication Data
US 2018/0289275 A1 Oct. 11, 2018

Related U.S. Application Data

(60) Division of application No. 15/432,811, filed on Feb. 14, 2017, now Pat. No. 10,022,062, which is a
(Continued)

(51) Int. Cl.
*A61B 5/00* (2006.01)
*A61N 1/04* (2006.01)
(Continued)

(52) U.S. Cl.
CPC ............ *A61B 5/002* (2013.01); *A61B 5/0002* (2013.01); *A61B 5/01* (2013.01); *A61B 5/0531* (2013.01);
(Continued)

(58) Field of Classification Search
CPC ... A61B 5/0424; A61B 5/6843; A61B 5/0531; A61B 5/01; A61B 5/002; A61B 5/0002;
(Continued)

(56) References Cited

U.S. PATENT DOCUMENTS 3,724,355 A 4/1973 Unger
4,576,170 A 3/1986 Bradley et al.
(Continued)

FOREIGN PATENT DOCUMENTS

WO 1998039061 A2 9/1998

OTHER PUBLICATIONS

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi:10.1093/eurheartj/eht167, European Society of Cardiology.
(Continued)

*Primary Examiner* — Catherine M Voorhees
(74) *Attorney, Agent, or Firm* — Spectrum IP Law Group LLC

(57) ABSTRACT

Patient electrodes, patient monitors, defibrillators, wearable defibrillators, software and methods may warn when an electrode stops being fully attached to the patient's skin. A patient electrode includes a pad for attaching to the skin of a patient, a lead coupled to the pad, and a contact detector that can change state, when the pad does not contact fully the
(Continued)

skin of the patient. When the detector changes state, an output device may emit an alert, for notifying a rescuer or even the patient.

15 Claims, 11 Drawing Sheets

Related U.S. Application Data division of application No. 14/956,776, filed on Dec. 2, 2015, now abandoned, which is a division of application No. 14/064,468, filed on Oct. 28, 2013, now Pat. No. 9,237,858, which is a continuation-in-part of application No. 13/024,225, filed on Feb. 9, 2011, now abandoned.

(60) Provisional application No. 61/875,600, filed on Sep. 9, 2013.

(51) Int. Cl.
  *A61B 5/01*      (2006.01)
  *A61B 5/0531*    (2021.01)
  *A61N 1/39*      (2006.01)
  *A61B 5/276*     (2021.01)
  *A61N 1/08*      (2006.01)

(52) U.S. Cl.
  CPC ............ *A61B 5/276* (2021.01); *A61B 5/6843* (2013.01); *A61B 5/742* (2013.01); *A61B 5/7405* (2013.01); *A61B 5/746* (2013.01); *A61B 5/7455* (2013.01); *A61N 1/046* (2013.01); *A61N 1/0492* (2013.01); *A61N 1/3904* (2017.08); *A61N 1/3925* (2013.01); *A61B 2560/0276* (2013.01); *A61N 2001/083* (2013.01)

(58) Field of Classification Search
  CPC ..... A61B 5/7455; A61B 5/742; A61B 5/7405; A61B 5/746; A61B 2560/0276; A61N 1/08; A61N 1/0492; A61N 1/3925; A61N 1/39; A61N 1/046; A61N 2001/083
  See application file for complete search history.

(56) References Cited

U.S. PATENT DOCUMENTS

| | | |
|---|---|---|
| 4,583,524 A | 4/1986 | Hutchins |
| 4,619,265 A | 10/1986 | Morgan et al. |
| 4,928,690 A | 5/1990 | Heilman et al. |
| 4,955,381 A | 9/1990 | Way et al. |
| 5,078,134 A | 1/1992 | Heilman et al. |
| 5,228,449 A | 7/1993 | Christ et al. |
| 5,348,008 A | 9/1994 | Bomn et al. |
| 5,353,793 A | 10/1994 | Bomn |
| RE34,800 E | 11/1994 | Hutchins |
| 5,394,892 A | 3/1995 | Kenny |
| 5,405,362 A | 4/1995 | Kramer et al. |
| 5,469,859 A * | 11/1995 | Tsoglin ............... A61B 5/0205 600/536 |
| 5,474,574 A | 12/1995 | Payne et al. |
| 5,662,690 A | 9/1997 | Cole et al. |
| 5,782,878 A | 7/1998 | Morgan et al. |
| 5,792,204 A | 8/1998 | Snell |
| 5,902,249 A | 5/1999 | Lyster |
| 5,913,685 A | 6/1999 | Hutchins |
| 5,944,669 A | 8/1999 | Kaib |
| 6,007,532 A | 12/1999 | Netherly |
| 6,047,203 A | 4/2000 | Sackner et al. |
| 6,065,154 A * | 5/2000 | Hulings ............... A61N 1/0484 2/102 |
| 6,108,197 A | 8/2000 | Janik |
| 6,148,233 A | 11/2000 | Owen et al. |
| 6,201,992 B1 | 3/2001 | Freeman |
| 6,263,238 B1 | 7/2001 | Brewer et al. |
| 6,287,328 B1 | 9/2001 | Snyder et al. |
| 6,304,780 B1 | 10/2001 | Owen et al. |
| 6,319,011 B1 | 11/2001 | Motti et al. |
| 6,334,070 B1 | 12/2001 | Nova et al. |
| 6,356,785 B1 | 3/2002 | Snyder |
| 6,427,083 B1 | 7/2002 | Owen et al. |
| 6,437,083 B1 | 8/2002 | Brack et al. |
| 6,529,875 B1 | 3/2003 | Nakajima |
| 6,546,285 B1 | 4/2003 | Owen et al. |
| 6,671,545 B2 | 12/2003 | Fincke |
| 6,681,003 B2 | 1/2004 | Linder et al. |
| 6,762,917 B1 | 7/2004 | Verbiest et al. |
| 7,065,401 B2 | 6/2006 | Worden |
| D543,976 S | 6/2007 | Oliver |
| 7,559,902 B2 | 7/2009 | Ting et al. |
| 7,792,577 B2 | 9/2010 | Hamilton et al. |
| 7,865,238 B2 | 1/2011 | Brink |
| 7,870,761 B2 | 1/2011 | Valentine et al. |
| 7,974,689 B2 | 7/2011 | Volpe et al. |
| 8,080,007 B2 * | 12/2011 | Dunning ............... A61B 18/16 606/32 |
| 8,135,462 B2 | 3/2012 | Owen et al. |
| 8,140,154 B2 | 3/2012 | Donnelly et al. |
| 8,242,907 B2 | 8/2012 | Butler et al. |
| 8,369,944 B2 | 2/2013 | Macho et al. |
| 8,451,119 B1 | 5/2013 | Rahimi et al. |
| 8,548,557 B2 | 10/2013 | Garstka et al. |
| 8,615,295 B2 | 12/2013 | Savage et al. |
| 8,644,925 B2 | 2/2014 | Volpe et al. |
| 8,897,860 B2 | 11/2014 | Volpe et al. |
| 8,904,214 B2 | 12/2014 | Volpe et al. |
| 8,965,500 B2 | 2/2015 | Macho et al. |
| 9,008,801 B2 | 4/2015 | Kaib et al. |
| 9,089,685 B2 | 7/2015 | Sullivan et al. |
| 9,131,901 B2 | 9/2015 | Volpe et al. |
| 9,132,267 B2 | 9/2015 | Kaib |
| 9,408,548 B2 | 8/2016 | Volpe et al. |
| 9,454,219 B2 | 9/2016 | Volpe et al. |
| 9,569,625 B2 * | 2/2017 | DiBona ............... G06Q 10/00 |
| 9,592,403 B2 | 3/2017 | Sullivan |
| 2003/0095648 A1 | 5/2003 | Kaib et al. |
| 2003/0158593 A1 | 8/2003 | Heilman et al. |
| 2004/0178913 A1 * | 9/2004 | Penuela ............... G01D 21/00 340/573.1 |
| 2005/0107833 A1 | 5/2005 | Freeman et al. |
| 2005/0107834 A1 | 5/2005 | Freeman et al. |
| 2005/0114154 A1 | 5/2005 | Wolkowicz et al. |
| 2006/0244568 A1 | 11/2006 | Tong et al. |
| 2007/0203407 A1 | 8/2007 | Hoss et al. |
| 2008/0197979 A1 | 8/2008 | Enyedy et al. |
| 2008/0303637 A1 | 12/2008 | Gelbman et al. |
| 2008/0312709 A1 | 12/2008 | Volpe et al. |
| 2009/0005827 A1 | 1/2009 | Weintraub et al. |
| 2009/0012381 A1 | 1/2009 | Kuramori |
| 2009/0248128 A1 | 10/2009 | Nassif et al. |
| 2010/0007413 A1 | 1/2010 | Herleikson |
| 2010/0109903 A1 | 5/2010 | Carrick |
| 2010/0194541 A1 | 8/2010 | Stevenson |
| 2010/0298899 A1 | 11/2010 | Donnelly et al. |
| 2011/0022105 A9 | 1/2011 | Owen et al. |
| 2011/0288604 A1 | 11/2011 | Kaib et al. |
| 2011/0288605 A1 | 11/2011 | Kaib et al. |
| 2011/0313311 A1 | 12/2011 | Gaw |
| 2012/0112903 A1 | 5/2012 | Kaib et al. |
| 2012/0116240 A1 | 5/2012 | Chou |
| 2012/0144551 A1 | 6/2012 | Guldalian |
| 2012/0150008 A1 | 6/2012 | Kaib et al. |
| 2012/0158075 A1 | 6/2012 | Kalb et al. |
| 2012/0197324 A1 | 8/2012 | Nova |
| 2012/0265265 A1 | 10/2012 | Razavi et al. |
| 2012/0283794 A1 | 11/2012 | Kaib et al. |
| 2012/0287671 A1 | 11/2012 | Parker et al. |
| 2012/0293323 A1 | 11/2012 | Kaib et al. |
| 2012/0302860 A1 | 11/2012 | Volpe et al. |
| 2012/0310315 A1 | 12/2012 | Savage et al. |
| 2013/0085538 A1 | 4/2013 | Volpe et al. |

(56) References Cited

U.S. PATENT DOCUMENTS

| | | |
|---|---|---|
| 2013/0116533 A1* | 5/2013 | Lian .................... A61B 5/0006 600/391 |
| 2013/0231711 A1 | 9/2013 | Kaib |
| 2013/0245388 A1* | 9/2013 | Rafferty ............... A61B 5/6833 600/301 |
| 2013/0274565 A1 | 10/2013 | Langer et al. |
| 2013/0317852 A1 | 11/2013 | Worrell et al. |
| 2013/0325078 A1 | 12/2013 | Whiting et al. |
| 2014/0025131 A1 | 1/2014 | Sullivan et al. |
| 2014/0070957 A1 | 3/2014 | Longinotti-Buitoni et al. |
| 2014/0163663 A1 | 6/2014 | Poddar et al. |
| 2014/0257422 A1* | 9/2014 | Herken ................ A61N 1/3925 607/8 |
| 2014/0324112 A1 | 10/2014 | Macho et al. |
| 2014/0378812 A1 | 12/2014 | Saroka et al. |
| 2015/0039053 A1 | 2/2015 | Kaib et al. |
| 2015/0328472 A1 | 11/2015 | Sullivan et al. |
| 2016/0004831 A1 | 1/2016 | Carlson et al. |
| 2016/0082277 A1 | 3/2016 | Foshee, Jr. et al. |

OTHER PUBLICATIONS

Lifecor LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

Heartstart MRx and XL AED Algorithm—Application Note, Jul. 2001, Edition 2 Philips Healthcare, USA.

The LifeVest Network/Patient Data Management System, Zoll, 2015, 20C0503 Rev A.

Pagan-Carlo, et al., "Encircling Overlapping Multipulse Shock Waveforms for Transthoracic Defibrillation," JACC Journals, Dec. 1998, vol. 32 Issue 7, p. 2065-2071.

* cited by examiner

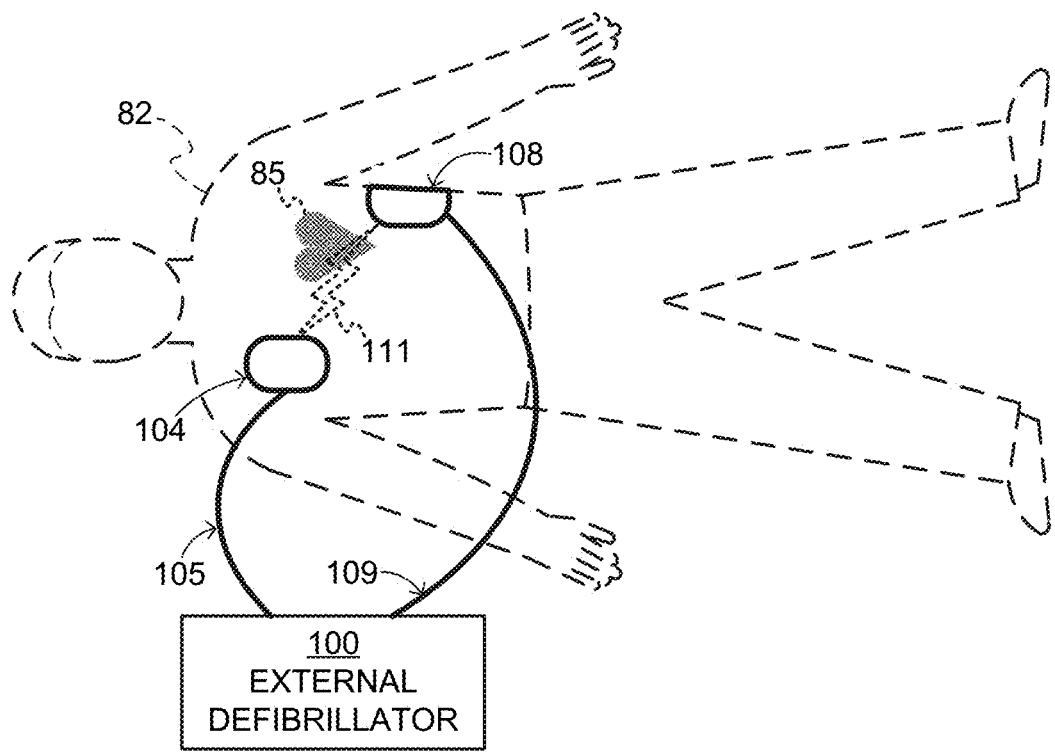
FIG. 1  *DEFIBRILLATION SCENE*
| TYPE OF EXTERNAL DEFIBRILLATOR | INTENDED TO BE USED BY PERSONS: | |
|---|---|---|
| | IN THE MEDICAL PROFESSIONS | NOT IN THE MEDICAL PROFESSIONS |
| DEFIBRILLATOR – MONITOR | √ | |
| AED | √ | √ |
FIG. 2  *TWO MAIN TYPES OF EXTERNAL DEFIBRILLATORS*

COMPONENTS OF PATIENT ELECTRODE WITH CONTACT SENSOR

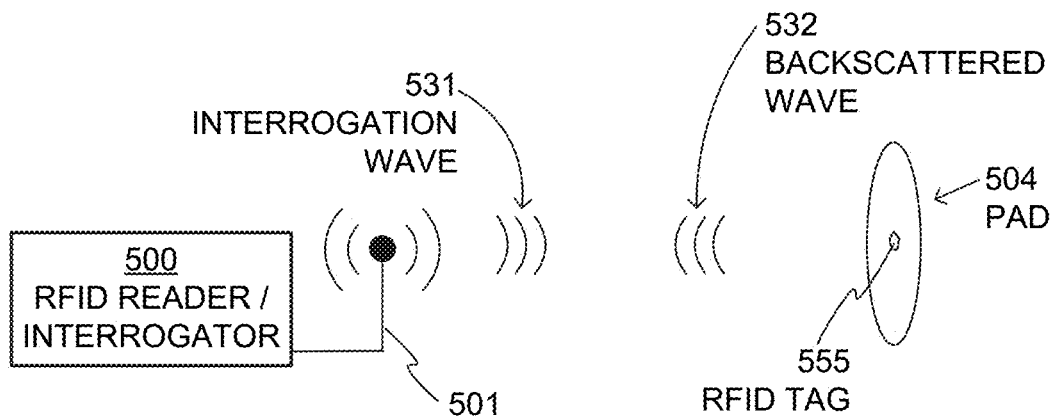
FIG. 5A — *WIRELESS SENSE SIGNAL AS RFID BACKSCATTER*
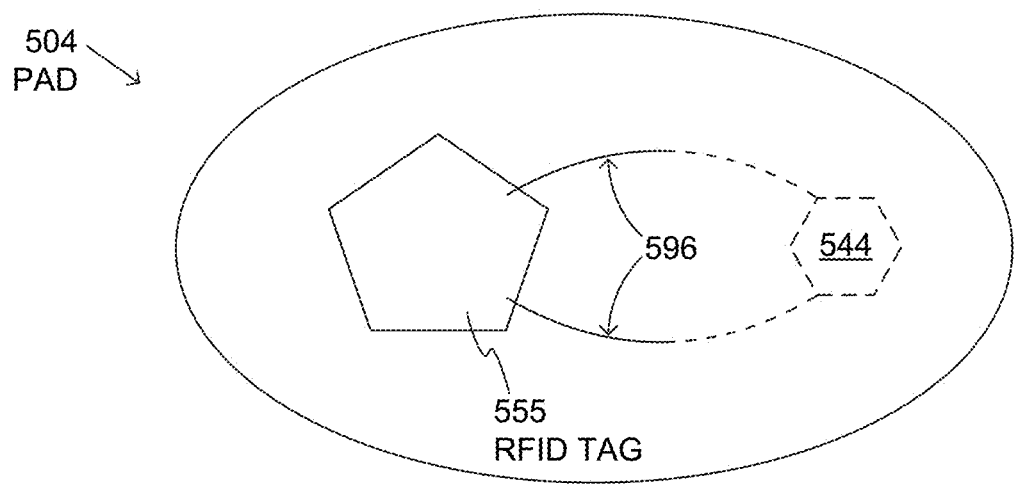
FIG. 5B — *ELECTRODE PAD WITH CONTACT SENSOR & RFID TAG*

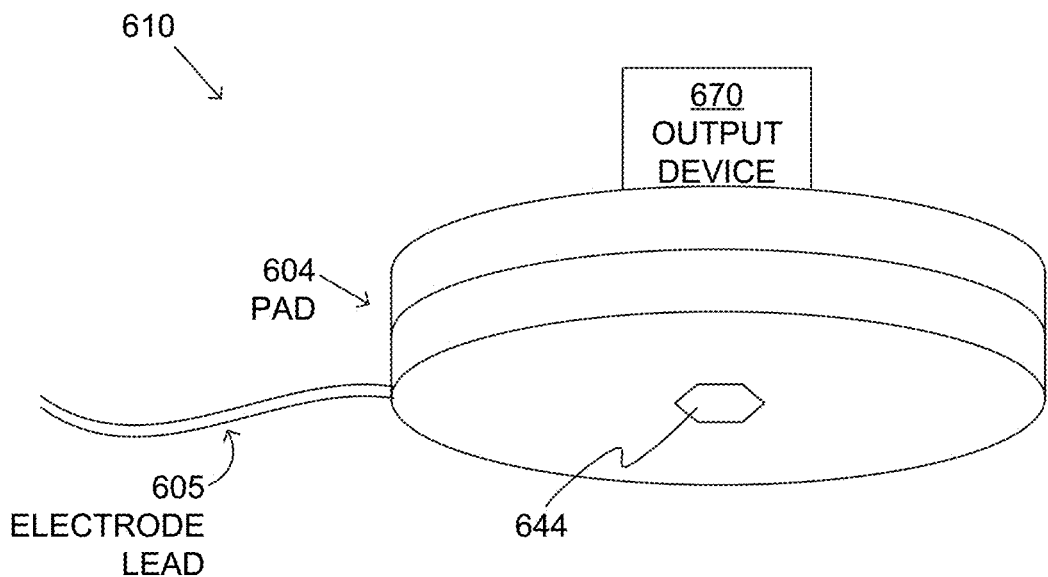
FIG. 6  *PATIENT ELECTRODE WITH CONTACT DETECTOR*
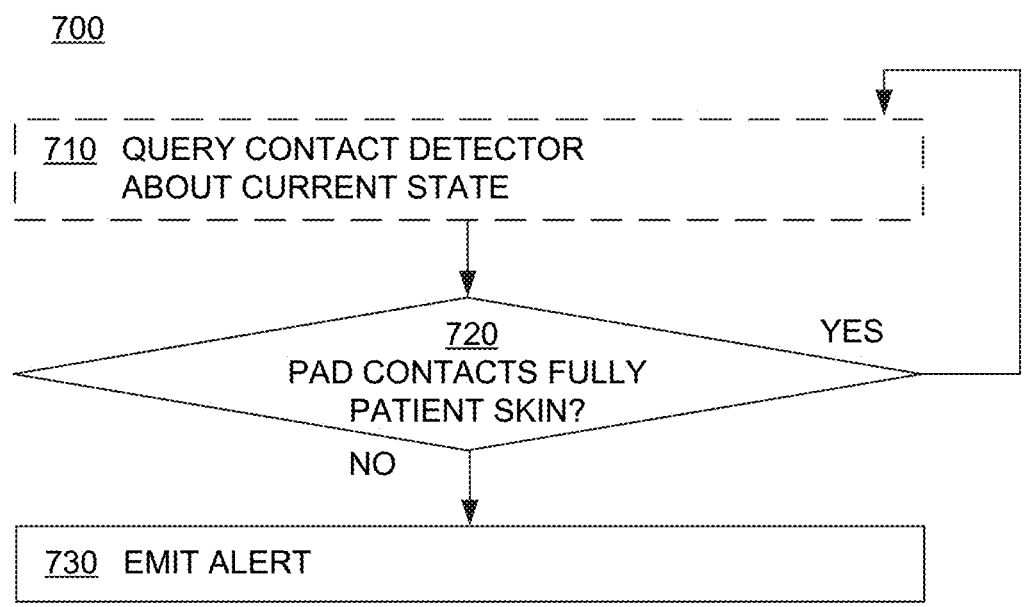
FIG. 7  *METHODS*

*HOST DEVICE THAT MAY USE PATIENT ELECTRODE WITH CONTACT SENSOR*

COMPONENTS OF
WEARABLE DEFIBRILLATOR SYSTEM

RFID-BASED WIRELESS SENSING OF CHANGED CONDITION

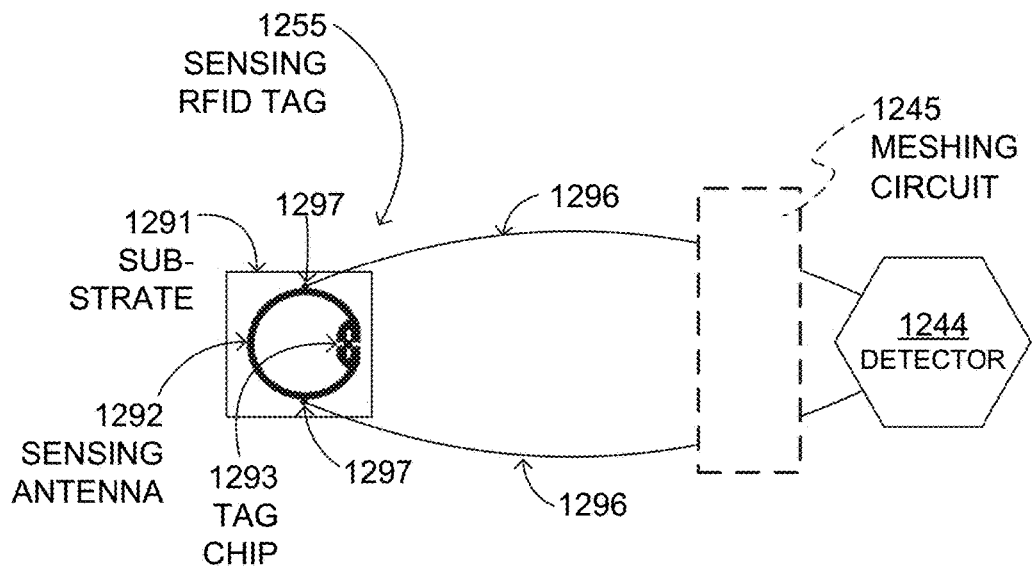
FIG. 12  *RFID-BASED SENSOR CONNECTIONS*
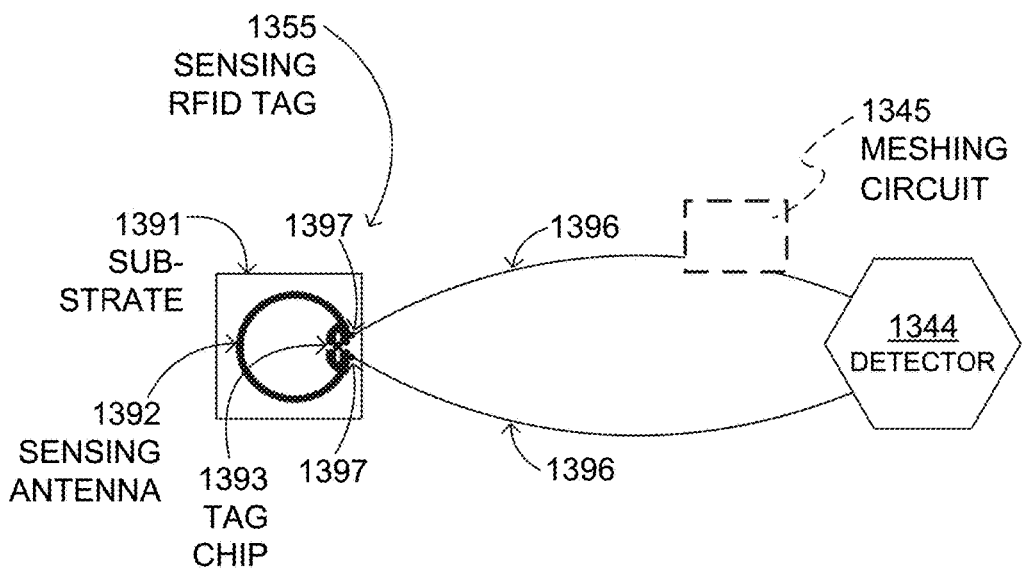
FIG. 13  *RFID-BASED SENSOR CONNECTIONS*

ALERTING FOR LOSS OF FULL SKIN CONTACT OF PATIENT ELECTRODES

CROSS REFERENCE TO RELATED PATENT APPLICATIONS

This patent application is a divisional of U.S. patent application Ser. No. 15/432,811 filed on Feb. 14, 2017, which in turn is a divisional of U.S. patent application Ser. No. 14/956,776 filed on Dec. 2, 2015 and is now abandoned, which in turn is a divisional of U.S. patent application Ser. No. 14/064,468 filed on Oct. 28, 2013 and issued on Jan. 19, 2016 as U.S. Pat. No. 9,237,858, which in turn claims priority from U.S. Provisional Patent Application Ser. No. 61/875,600, filed on Sep. 9, 2013, and which further is a Continuation-In-Part of U.S. patent application Ser. No. 13/024,225, filed on Feb. 9, 2011, and is now abandoned.

This patent application may be found to be related with U.S. patent application Ser. No. 14/064,515, filed on Oct. 28, 2013 and issued on Apr. 19, 2016 as U.S. Pat. No. 9,317,729.

BACKGROUND

In humans, the heart beats to sustain life. In normal operation, it pumps blood through the various parts of the body. More particularly, the various chambers of the heart contract and expand in a periodic and coordinated fashion, which causes the blood to be pumped regularly. More specifically, the right atrium sends deoxygenated blood into the right ventricle. The right ventricle pumps the blood to the lungs, where it becomes oxygenated, and from where it returns to the left atrium. The left atrium pumps the oxygenated blood to the left ventricle. The left ventricle then expels the blood, forcing it to circulate to the various parts of the body.

The heart chambers pump because of the heart's electrical control system. More particularly, the sinoatrial (SA) node generates an electrical impulse, which generates further electrical signals. These further signals cause the above-described contractions of the various chambers in the heart, in the correct sequence. The electrical pattern created by the sinoatrial (SA) node is called a sinus rhythm.

Sometimes, however, the electrical control system of the heart malfunctions, which can cause the heart to beat irregularly, or not at all. The cardiac rhythm is then generally called an arrhythmia. Arrhythmias may be caused by electrical activity from locations in the heart other than the SA node. Some types of arrhythmia may result in inadequate blood flow, thus reducing the amount of blood pumped to the various parts of the body. Some arrhythmias may even result in a Sudden Cardiac Arrest (SCA). In a SCA, the heart fails to pump blood effectively, and, if not treated, death can occur. In fact, it is estimated that SCA results in more than 250,000 deaths per year in the United States alone. Further, a SCA may result from a condition other than an arrhythmia.

One type of arrhythmia associated with SCA is known as Ventricular Fibrillation (VF). VF is a type of malfunction where the ventricles make rapid, uncoordinated movements, instead of the normal contractions. When that happens, the heart does not pump enough blood to deliver enough oxygen to the vital organs. The person's condition will deteriorate rapidly and, if not reversed in time, they will die soon, e.g. within ten minutes.

Ventricular Fibrillation can often be reversed using a life-saving device called a defibrillator. A defibrillator, if applied properly, can administer an electrical shock to the heart. The shock may terminate the VF, thus giving the heart the opportunity to resume pumping blood. If VF is not terminated, the shock may be repeated, often at escalating energies.

A challenge with defibrillation is that the electrical shock must be administered very soon after the onset of VF. There is not much time: the survival rate of persons suffering from VF decreases by about 10% for each minute the administration of a defibrillation shock is delayed. After about 10 minutes, the rate of survival for SCA victims averages less than 2%.

The challenge of defibrillating early after the onset of VF is being met in a number of ways. First, for some people who are considered to be at a higher risk of VF or other heart arrythmias, an Implantable Cardioverter Defibrillator (ICD) can be implanted surgically. An ICD can monitor the person's heart, and administer an electrical shock as needed. As such, an ICD reduces the need to have the higher-risk person be monitored constantly by medical personnel.

Regardless, VF can occur unpredictably, even to a person who is not considered at risk. As such, VF can be experienced by many people who lack the benefit of ICD therapy. When VF occurs to a person who does not have an ICD, they collapse, because blood flow has stopped. They should receive therapy quickly.

For a VF victim without an ICD, a different type of defibrillator can be used, which is called an external defibrillator. External defibrillators have been made portable, so they can be brought to a potential VF victim quickly enough to revive them by a rescuer. For a person at extremely high risk of VF, wearable defibrillators have been made A problem with defibrillators is that they have electrodes that could fall off the patient. The electrodes could lose contact with the skin of the patient, which prevents them from acquiring an ECG of the patient, and then guiding an electrical shock for defibrillating the patient.

In addition, in the field of sensing, sometimes some locations are not easily accessible. Radio Frequency Identification (RFID) tags offer advantages for labeling items and being sensed remotely, but it is often not economical to produce small numbers of custom RFID tags for very specific purposes.

BRIEF SUMMARY

The present description gives instances of patient electrodes, patient monitors, defibrillators, wearable defibrillators, software and methods, the use of which may help overcome problems and limitations of the prior art.

In one embodiment, a patient electrode includes a pad for attaching to the skin of a patient, a lead coupled to the pad, and a contact detector that can change state, when the pad does not contact fully the skin of the patient. When the detector changes state, an output device may emit an alert, for notifying a rescuer or even the patient. An advantage over the prior art is that embodiments can be made economically.

These and other features and advantages of this description will become more readily apparent from the following Detailed Description, which proceeds with reference to the drawings, in which:

BRIEF DESCRIPTION OF THE DRAWINGS

FIG. 1 is a diagram of a scene where an external defibrillator is used to save the life of a person according to embodiments.

FIG. 2 is a table listing two main types of the external defibrillator shown in FIG. 1, and who they might be used by.

FIGS. 5A and 5B are diagrams of embodiments of novel use of RFID technology, applied to embodiments of the novel electrodes and systems of the invention.

FIG. 6 is a diagram of a patient electrode according to an embodiment where an output device is coupled to the electrode.

FIG. 7 is a flowchart for illustrating methods according to embodiments.

FIG. 12 is a diagram illustrating electrical connections for an RFID-based sensor, according to embodiments that can be used to mainly detune the tag antenna as a result of sensing a changed condition.

FIG. 13 is a diagram illustrating electrical connections for an RFID-based sensor, according to embodiments that can be used mainly to disrupt the tag chip operation as a result of sensing a changed condition.

DETAILED DESCRIPTION

Figure 3:
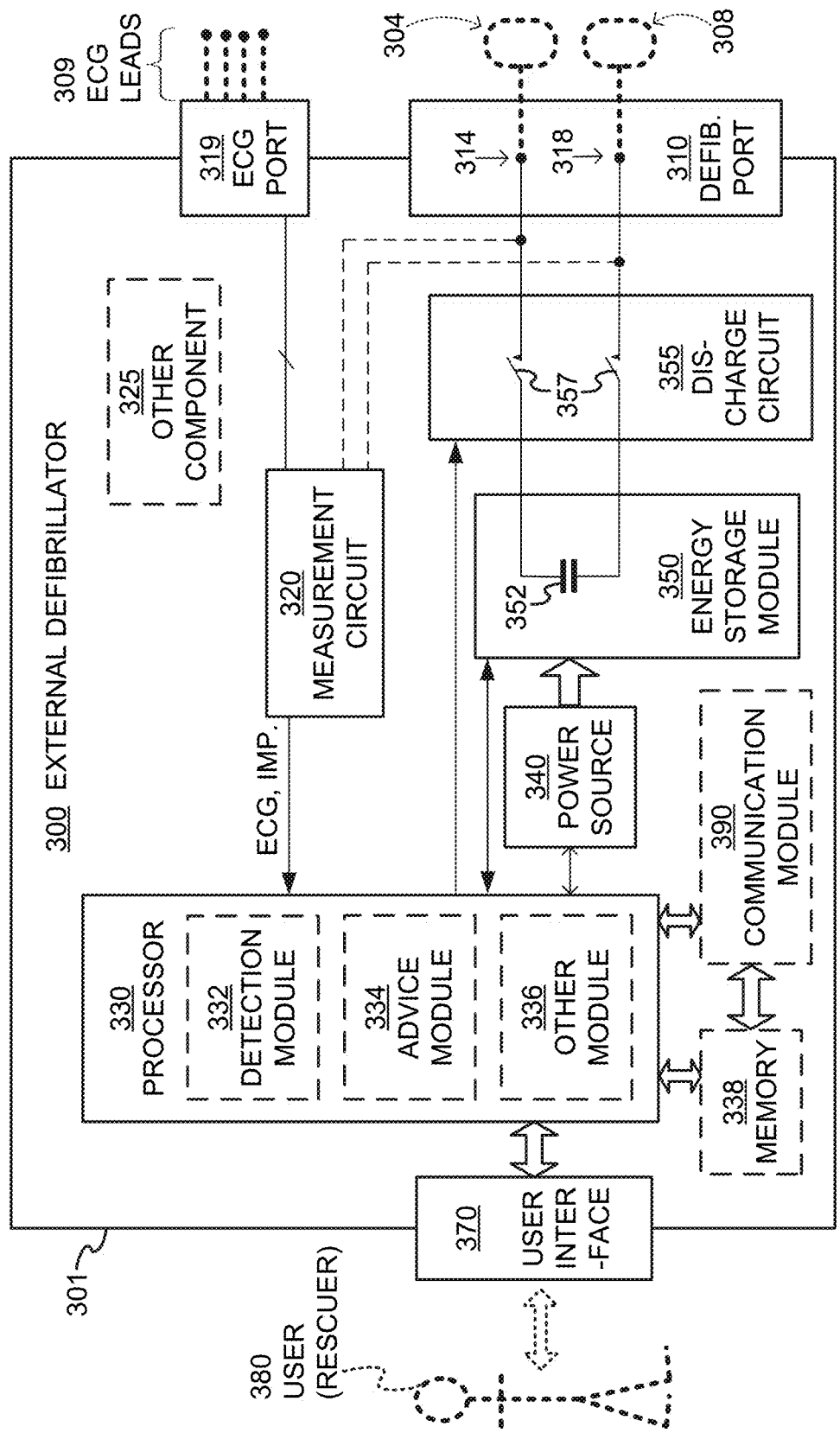
FIG. 3 is a diagram showing components of an external defibrillator, such as the one shown in FIG. 1, which is made according to embodiments.

As have been mentioned, the present description is about inventions in both fields of defibrillation and RFID, which have overlap. Embodiments of the inventions are now described in more detail. This specification should be interpreted as a whole, and not as separated by the subheadings below.

Detecting Loss of Full Skin Contact in Patient Electrodes

FIG. 1 is a diagram of a defibrillation scene. A person 82 is lying on their back. Person 82 could be a patient in a hospital, or someone found unconscious, and then turned to be on their back. Person 82 is experiencing a condition in their heart 85, which could be Ventricular Fibrillation (VF).

A portable external defibrillator 100 has been brought close to person 82. At least two defibrillation electrodes are usually provided with external defibrillator 100, and are sometimes called electrodes. The first electrode is made of a pad 104 and electrode lead 105, and the second electrode is made of a pad 108 and electrode lead 109. At least one of these electrodes has a further component according to embodiments. A rescuer (not shown) has attached pads 104, 108 to the skin of person 82. Defibrillator 100 is administering, via the electrodes, a brief, strong electric pulse 111 through the body of person 82. Pulse 111, also known as a defibrillation shock, goes also through heart 85, in an attempt to restart it, for saving the life of person 82.

Defibrillator 100 can be one of different types, each with different sets of features and capabilities. The set of capabilities of defibrillator 100 is determined by planning who would use it, and what training they would be likely to have. Examples are now described.

FIG. 2 is a table listing two main types of external defibrillators, and who they are primarily intended to be used by. A first type of defibrillator 100 is generally called a defibrillator-monitor, because it is typically formed as a single unit in combination with a patient monitor. A defibrillator-monitor is sometimes called monitor-defibrillator. A defibrillator-monitor is intended to be used by persons in the medical professions, such as doctors, nurses, paramedics, emergency medical technicians, etc. Such a defibrillator-monitor is intended to be used in a pre-hospital or hospital scenario.

As a defibrillator, the device can be one of different varieties, or even versatile enough to be able to switch among different modes that individually correspond to the varieties. One variety is that of an automated defibrillator, which can determine whether a shock is needed and, if so, charge to a predetermined energy level and instruct the user to administer the shock. Another variety is that of a manual defibrillator, where the user determines the need and controls administering the shock.

As a patient monitor, the device has features additional to what is minimally needed for mere operation as a defibrillator. These features can be for monitoring physiological indicators of a person in an emergency scenario. These physiological indicators are typically monitored as signals. For example, these signals can include a person's full ECG (electrocardiogram) signals, or impedance between two electrodes. Additionally, these signals can be about the person's temperature, non-invasive blood pressure (NIBP), arterial oxygen saturation/pulse oximetry (SpO2), the concentration or partial pressure of carbon dioxide in the respiratory gases, which is also known as capnography, and so on. These signals can be further stored and/or transmitted as patient data.

A second type of external defibrillator 100 is generally called an AED, which stands for "Automated External Defibrillator". An AED typically makes the shock/no shock determination by itself, automatically. Indeed, it can sense enough physiological conditions of the person 82 via only the shown defibrillation electrodes 104, 108 of FIG. 1. In its present embodiments, an AED can either administer the shock automatically, or instruct the user to do so, e.g. by pushing a button. Being of a much simpler construction, an AED typically costs much less than a defibrillator-monitor. As such, it makes sense for a hospital, for example, to deploy AEDs at its various floors, in case the more expensive defibrillator-monitor is more critically being deployed at an Intensive Care Unit, and so on.

AEDs, however, can also be used by people who are not in the medical professions. More particularly, an AED can be used by many professional first responders, such as policemen, firemen, etc. Even a person with first-aid and CPR/AED training can use one. And AEDs increasingly can supply instructions to whoever is using them.

AEDs are thus particularly useful, because it is so critical to respond quickly, when a person suffers from VF. Indeed, the people who will first reach the VF sufferer may not be in the medical professions.

Increasing awareness has resulted in AEDs being deployed in public or semi-public spaces, so that even a member of the public can use one, if they have obtained first aid and CPR/AED training on their own initiative. This way, defibrillation can be administered soon enough after the onset of VF, to hopefully be effective in rescuing the person.

There are additional types of external defibrillators, which are not listed in FIG. 2. For example, a hybrid defibrillator can have aspects of an AED, and also of a defibrillator-monitor. A usual such aspect is additional ECG monitoring capability. A wearable defibrillator is another example.

FIG. 3 is a diagram showing components of an external defibrillator 300 made according to embodiments. These components can be, for example, in external defibrillator 100 of FIG. 1. These components of FIG. 3 can be provided in a housing 301, which is also known as casing 301.

External defibrillator 300 is intended for use by a user 380, who would be the rescuer. Defibrillator 300 typically includes a defibrillation port 310, such as a socket in housing 301. Defibrillation port 310 includes nodes 314, 318. Defibrillation electrodes 304, 308, which can be similar to the electrodes of FIG. 1, can be plugged in defibrillation port 310, so as to make electrical contact with nodes 314, 318, respectively. It is also possible that electrodes can be connected continuously to defibrillation port 310, etc. Either way, defibrillation port 310 can be used for guiding via electrodes to person 82 an electrical charge that has been stored in defibrillator 300, as will be seen later in this document.

If defibrillator 300 is actually a defibrillator-monitor, as was described with reference to FIG. 2, then it will typically also have an ECG port 319 in housing 301, for plugging in ECG electrode leads 309. ECG electrode leads 309 can help sense an ECG signal, e.g. a 12-lead signal, or from a different number of leads. Moreover, a defibrillator-monitor could have additional ports (not shown), and an other component 325 for the above described additional features, such as patient signals.

Defibrillator 300 also includes a measurement circuit 320. Measurement circuit 320 receives physiological signals from ECG port 319, and also from other ports, if provided. These physiological signals are sensed, and information about them is rendered by circuit 320 as data, or other signals, etc.

If defibrillator 300 is actually an AED, it may lack ECG port 319. Measurement circuit 320 can obtain physiological signals through nodes 314, 318 instead, when defibrillation electrodes 304, 308 are attached to person 82. In these cases, a person's ECG signal can be sensed as a voltage difference between electrodes 304, 308. Plus, impedance between electrodes 304, 308 can be sensed for detecting, among other things, whether these electrodes 304, 308 have been inadvertently disconnected from the person, above and beyond the present invention, or in combination with the present invention.

Defibrillator 300 also includes a processor 330. Processor 330 may be implemented in any number of ways. Such ways include, by way of example and not of limitation, digital and/or analog processors such as microprocessors and digital-signal processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 330 can be considered to have a number of modules. One such module can be a detection module 332, which senses outputs of measurement circuit 320. Detection module 332 can include a VF detector. Thus, the person's sensed ECG can be used to determine whether the person is experiencing VF.

Another such module in processor 330 can be an advice module 334, which arrives at advice based on outputs of detection module 332. Advice module 334 can include a Shock Advisory Algorithm, implement decision rules, and so on. The advice can be to shock, to not shock, to administer other forms of therapy, and so on. If the advice is to shock, some external defibrillator embodiments merely report that to the user, and prompt them to do it. Other embodiments further execute the advice, by administering the shock. If the advice is to administer CPR, defibrillator 300 may further issue prompts for it, and so on.

Processor 330 can include additional modules, such as module 336, for other functions. In addition, if other component 325 is indeed provided, it may be operated in part by processor 330, etc.

Defibrillator 300 optionally further includes a memory 338, which can work together with processor 330. Memory 338 may be implemented in any number of ways. Such ways include, by way of example and not of limitation, nonvolatile memories (NVM), read-only memories (ROM), random access memories (RAM), any combination of these, and so on. Memory 338, if provided, can include programs for processor 330, and so on. The programs can be operational for the inherent needs of processor 330, and can also include protocols and ways that decisions can be made by advice module 334. In addition, memory 338 can store prompts for user 380, etc. Moreover, memory 338 can store patient data.

Defibrillator 300 may also include a power source 340. To enable portability of defibrillator 300, power source 340 typically includes a battery. Such a battery is typically implemented as a battery pack, which can be rechargeable or not. Sometimes, a combination is used, of rechargeable and non-rechargeable battery packs. Other embodiments of power source 340 can include AC power override, for where AC power will be available, and so on. In some embodiments, power source 340 is controlled by processor 330.

Defibrillator 300 additionally includes an energy storage module 350. Module 350 is where some electrical energy is stored, when preparing it for sudden discharge to administer a shock. Module 350 can be charged from power source 340 to the right amount of energy, as controlled by processor 330. In typical implementations, module 350 includes one or more capacitors 352, and so on.

Defibrillator 300 moreover includes a discharge circuit 355. Circuit 355 can be controlled to permit the energy stored in module 350 to be discharged to nodes 314, 318, and thus also to defibrillation electrodes 304, 308. Circuit 355 can include one or more switches 357. Those can be made in a number of ways, such as by an H-bridge, and so on.

Defibrillator 300 further includes a user interface 370 for user 380. User interface 370 can be made in any number of ways. For example, interface 370 may include a screen, to display what is detected and measured, provide visual feedback to the rescuer for their resuscitation attempts, and so on. Interface 370 may also include a speaker, to issue voice prompts, etc. Interface 370 may additionally include various controls, such as pushbuttons, keyboards, and so on. In addition, discharge circuit 355 can be controlled by processor 330, or directly by user 380 via user interface 370, and so on.

Defibrillator 300 can optionally include other components. For example, a communication module 390 may be provided for communicating with other machines. Such communication can be performed wirelessly, or via wire, or by infrared communication, and so on. This way, data can be communicated, such as patient data, incident information, therapy attempted, CPR performance, and so on.

Figure 4:
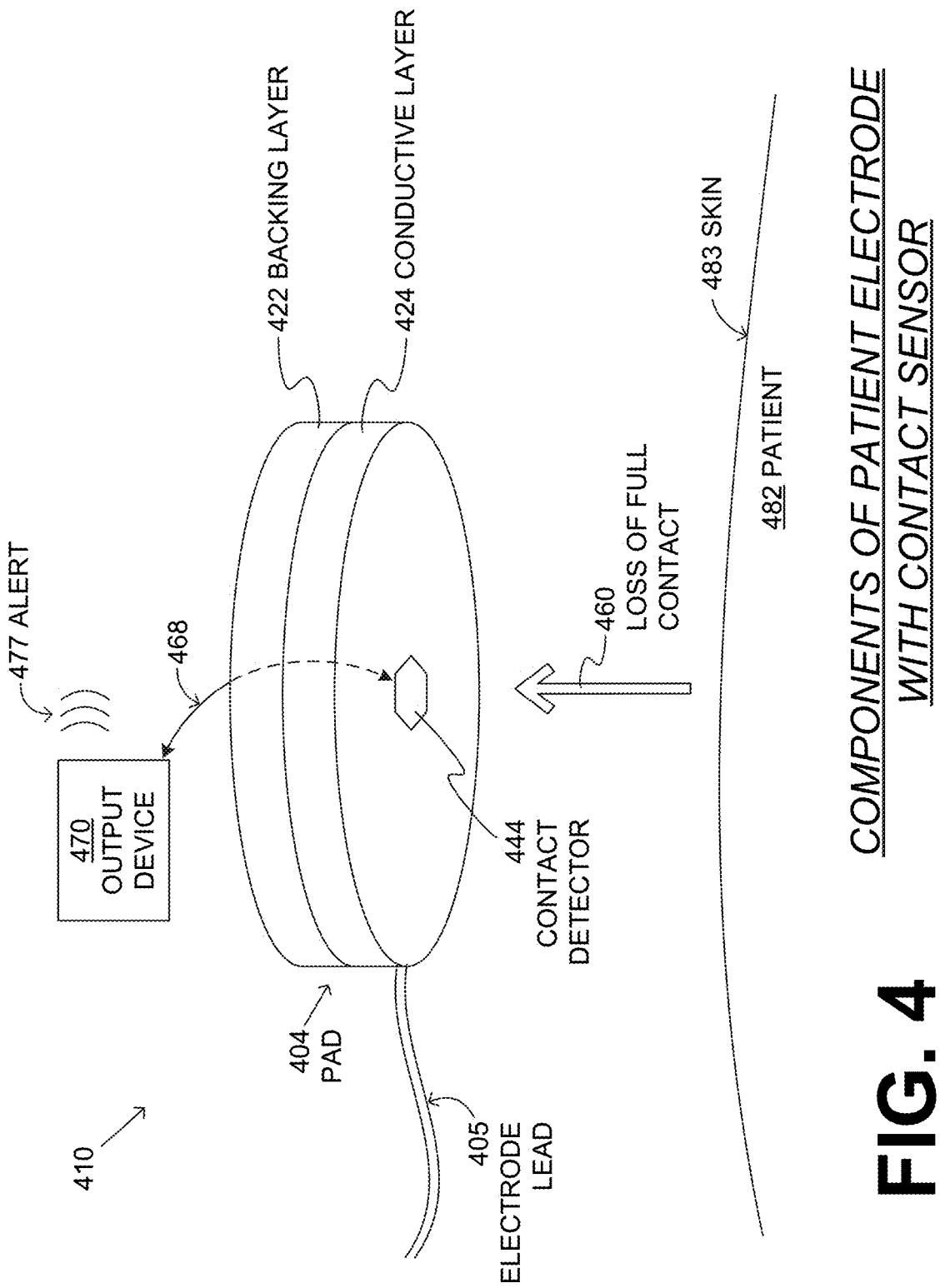
FIG. 4 is a diagram of components of a patient electrode made according to embodiments, in a use context.

FIG. 4 is a diagram of components of a patient electrode 410 made according to embodiments, in a use context. Patient electrode 410 includes a pad 404, which is configured to be attached to a skin 483 of a patient 482. Patient electrode 410 may also include an electrode lead 405 that is coupled to pad 404. A plug (not shown) may optionally be provided, coupled to electrode lead 405, and configured to be plugged into a socket, such as defibrillation port 310 or ECG port 319 of FIG. 3.

In some embodiments, patient electrode 410 is configured to detect an ECG signal of patient 482, when attached to skin 483. In some embodiments, patient electrode 410 is configured to deliver a defibrillation pulse to patient 482 through skin 483. In some embodiments, patient electrode 410 can do both. In other words, patient electrode 410 may be an ECG electrode, or a defibrillation electrode, or both.

Pad 404 can be flexible, to conform to the curvature of the body of patient 482. Pad 404 may include a backing layer 422, and a conductive layer 424 attached to backing layer 422. Conductive layer 424 is electrically coupled to electrode lead 405.

Conductive layer 424 typically has adhesive, for adhering to skin 483. Even though adhesives are good and help the entire pad 404 remain attached to skin 483, sometimes there is loss of full contact 460. Loss of full contact means that pad 404 does not contact skin 483 in part, or fully. Either only a portion, or the entire pad 404, may come off skin 483, neither of which is desirable. Defibrillating through a pad that has partially come off can increase the current density through the portion of the pad that has not come off, which can harm the patient. Alternately, some of the energy might not reach the patient depending on the electrode. And, if the pad has only partially come off, an ECG might still be received, thus possibly not alerting a user that the pad has partially come off.

Patient electrode 410 may also include a contact detector 444. Contact detector 444 may be coupled to pad 404 or electrode lead 405. Contact detector 444 may be configured to be in one of a plurality of detector states. In some embodiments, contact detector 444 can change from one state to another, when pad 404 does not contact fully skin 483. In some embodiments, the detector states are different values of an electrical property of the contact detector. The electrical property can be impedance, or generation of electrical current or voltage, and so on.

In some instances, a determination is made from the current detector state that pad 404 does not fully contact patient skin 483. This can be accomplished in a number of ways, which depend on the type of contact detector 444. Some examples are described, which are not limiting. In addition, more than one detection techniques can be used.

In some embodiments, contact detector 444 is a temperature sensor, and the detector state indicates a detected temperature. Normally, the detected temperature would be that of the patient's skin 483. However, if there is loss of contact 460, the temperature sensor will sense the temperature of the environment of skin 483, instead of that of skin 483 itself. Accordingly, the determination of loss of full contact 460 can then be made if the detected temperature changes beyond a threshold, or changes beyond a threshold within a preset time. Adjustments should be made for the event that the patient is being cooled, as will be obvious to a person skilled in the art in view of the present description.

In some embodiments, contact detector 444 is an optical sensor, and the detector state indicates a detected illumination. The optical sensor can be placed so that, when the pad is normally attached to skin 483, it prevents any light from reaching it. However, if there is loss of full contact 460, the optical sensor may detect illumination, which is the same phenomenon as lifting a curtain in an otherwise dark room. Accordingly, the determination of loss of full contact 460 can then be made if the detected illumination changes beyond a threshold.

In some embodiments, contact detector 444 is a capacitive sensor, and the detector state indicates a detected capacitance. The capacitive sensor can be placed so that, when the pad is normally attached to skin 483, the capacitive sensor detects capacitance from the mass of the patient 482. However, if there is loss of full contact 460, the capacitive sensor may detect a lot less capacitance, as it will not be detecting the capacitance from the mass of the patient 482. Accordingly, the determination of loss of full contact 460 can then be made if the detected capacitance changes beyond a threshold.

Patient electrode 410 is intended for use with an output device 470. Output device 470 is configured to emit an alert 477, when it is determined from the current detector state that pad 404 does not contact fully skin 483 of patient 482. The types of alert 477 are described later in this document.

Output device 470 may be implemented in any number of ways. It may be attached to patient electrode 410 or not. In some embodiments, output device 470 is coupled to a monitor that has a module configured to measure a physiological parameter of patient 482. In those cases, output device 470 can be used to emit another alert, if the physiological parameter exceeds a threshold or rescuers are to be notified.

In some embodiments, a sense signal is generated that encodes the current detector state. Output device 470 can be configured to receive a version of the sense signal, for example along path 468 in FIG. 4.

In some of those embodiments, patient electrode 410 further has a power source (not shown). The power source can be configured to query the contact detector about its current state, and generate the sense signal accordingly.

The sense signal can be implemented in any number of ways. It can be wired, in which case path 468 includes at least one wire. The wire can be implemented as a pair of sense leads, an example of which is shown later. Alternately, the wire can be implemented via electrode lead 405, by multiplexing its function between receiving ECG and sensing the detector. Moreover, the sense signal can be wireless, in which case path 468 includes the air. A number of wireless technologies may be used, such as Bluetooth and so on.

This description also includes inventions in the field of Radio Frequency IDentification (RFID) technology, which can be applied in many fields of remote sensing. Such inventions are described more fully later in this document, while some of their particular applications for the patient electrodes and systems of the invention are now described.

FIGS. 5A and 5B are diagrams of embodiments of novel use of RFID technology, applied to embodiments of the novel electrodes and systems of the invention. They are also an example where a sense signal is transmitted wirelessly according to embodiments. A patient electrode according to embodiments has a pad 504, a contact detector 544 shown only in FIG. 5B, and an RFID tag 555 coupled to contact detector 544.

In FIG. 5A, an RFID reader/interrogator 500 is configured to interrogate RFID tag 555. Reader 500 could be, for example, communication module 390 of FIG. 3. Reader 500 has an antenna 501, and transmits an interrogation wave 531. Tag 555 backscatters a backscattered wave 532, with information from tag 555. In such embodiments, backscattered wave 532 can encode the sense signal.

FIG. 5B shows more detail for pad 504. RFID tag 555 is located on the top side of pad 504, which does not contact the patient skin. Contact detector 544 is located on the bottom side of pad 504, which is why it is shown in dashed lines. Moreover, contact detector 544 is coupled to RFID tag 555 with jumper wires 596, which can go through pad 504, or around an edge of it. Briefly, as contact detector 544 detects that the pad does not contact fully the skin of the patient, its electrical properties will change, and thus operation of RFID tag 555 will be impacted. Accordingly, reader 500 may be able to detect the loss of contact, by comparing backscattered wave 532 with what it expected to receive. More detailed embodiments and explanations are provided later in this description.

As mentioned above, in some embodiments, the output device is coupled to the electrode. An example is now described.

FIG. 6 is a diagram of a patient electrode 610 according to embodiments. Electrode 610 has a pad 604, an electrode lead 605, and a contact detector 644. Electrode 610 also includes an output device 670 is coupled to pad 604. Alternately, output device 670 can be coupled to electrode lead 605.

The output device, such as output device 670, is made according to the alert that is desired. For example, the alert can be auditory, and output device 670 can include a sound producing device, such as a speaker. Or, the alert may be visual, and output device 670 can include a light producing device, such as a screen that can produce a message, an LED that can light next to appropriate writing, or picture, and so on. Or, the alert may be tactile, and output device 670 can include a vibrating mechanism.

FIG. 7 shows a flowchart 700 for describing methods according to embodiments. The methods of flowchart 700 may also be practiced by embodiments described above, such as the patient electrode of FIG. 6.

According to an optional operation 710, the contact detector of the patient electrode is queried about its current state. Optionally, a sense signal is generated responsive to the current detector state.

According to another operation 720, it is determined from the current state whether the pad contacts fully the skin of the patient. If a sense signal has been generated, the determination may be made from the sense signal. If the determination of operation 720 results in "yes", execution returns to operation 710.

If the determination of operation 720 results in "no", then according to another operation 730, an alert is emitted by the output device. In some embodiments, the output device receives a version of the sense signal, and emits the alert. In some embodiments, the alert signal is null unless operation 720 results in "no". Then the output device only operates based on the sense signal being non-zero.

Figure 8:
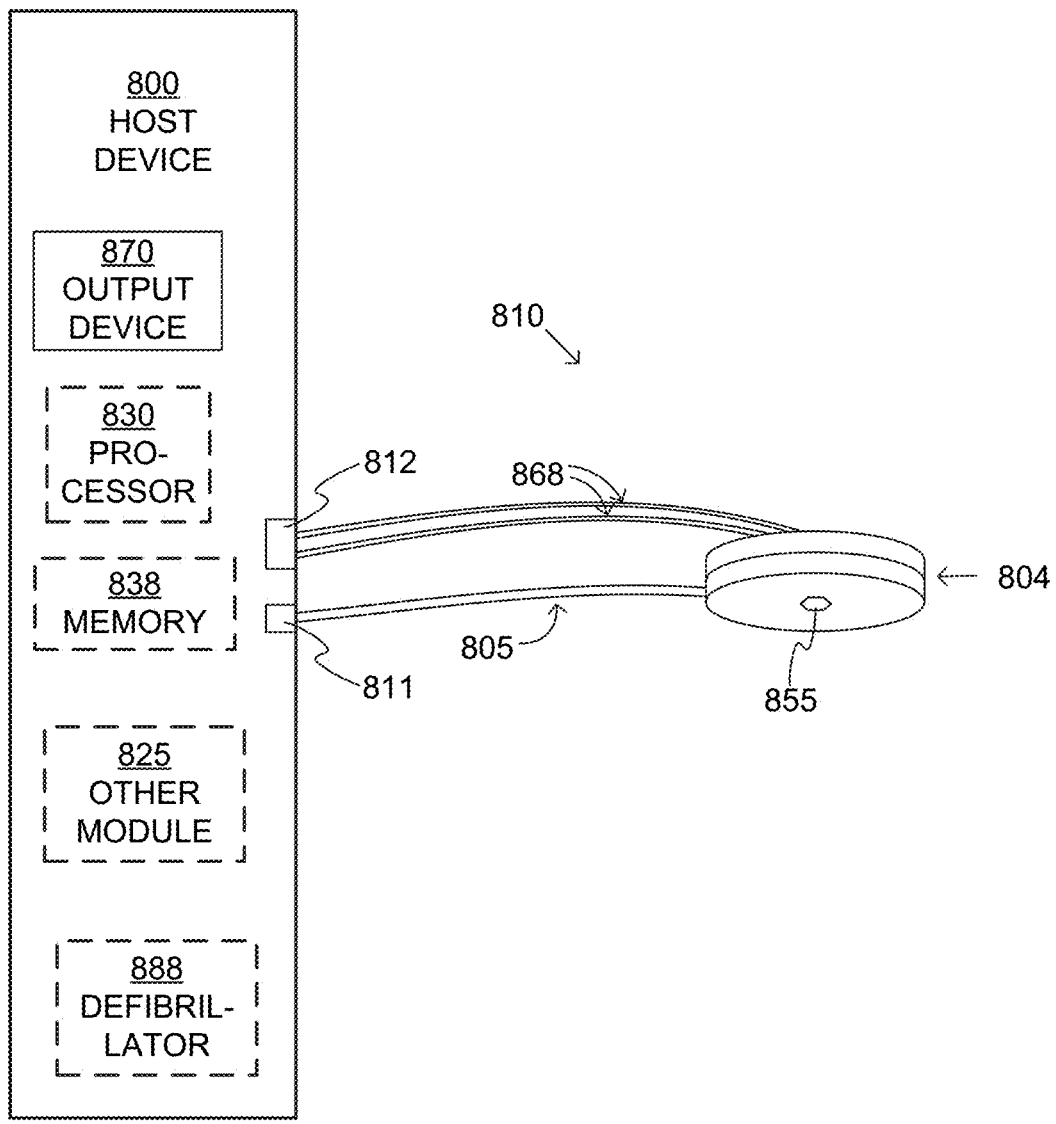
FIG. 8 is a diagram of a host device that may use an electrode according to embodiments.

FIG. 8 is a diagram of a host device 800 made according to embodiments, which may use an electrode 810 according to embodiments. Host device 800 may be a patient monitor, a defibrillator, a wearable defibrillator, a device such as that of FIG. 3, and so on. Patient electrode 810 includes a pad 804, an electrode lead 805 and a contact detector 855.

Host device 800 includes an electrode port 811. Electrode port 811 is configured to receive electrode lead 805. As electrode port 811 can be repeated for the proper number of electrodes, it will become similar to port 310 or port 319 of FIG. 3. Optionally, host device 800 could also have a module configured to measure an ECG of the patient through electrode port 811, such as module 320 of FIG. 3.

Host device 800 also includes a sense port 812. Sense port 812 is configured to receive a sense signal from contact detector 855.

In the embodiment of FIG. 8, electrode 810 includes sense leads 868, and sense port 812 is a physical port for receiving sense leads 868. The sense signal is thus transferred from electrode 810 via sense leads 868 to host device 800. Equivalently, the sense signal could be transferred wirelessly as seen in FIG. 5A, in which case sense port 812 is a wireless receiver such as reader 500 or communication module 390 of FIG. 3.

Host device 800 further includes an output device 870. Output device 870 is configured to emit an alert, if it is detected from the sense signal that pad 804 does not contact fully the skin of the patient.

Optionally, host device 800 may also include other components. For example, it may include a processor 830. Processor 830 may be configured to detect from the sense signal whether electrode 810 does not contact fully the skin of the patient.

Host device 800 may further include a memory 838, which can work together with processor 830. Memory 838 may be implemented in any number of ways. Such ways include, by way of example and not of limitation, volatile memories, nonvolatile memories (NVM), read-only memories (ROM), random access memories (RAM), magnetic disk storage media, optical storage media, smart cards, flash memory devices, any combination of these, and so on. Memory 838 is thus a non-transitory storage medium. Memory 838, if provided, can include programs for processor 830 to execute. Executing is performed by physical manipulations of physical quantities, and may result in the functions, processes and/or methods to be performed, and/or the processor to cause other devices or components or blocks to perform such functions, processes, actions and/or methods. The programs can include sets of instructions. The programs can be operational for the inherent needs of processor 830.

In addition, memory 838 can store prompts for a user. Moreover, memory 838 can store data. The data can include patient data, system data and environmental data. The data can be stored in memory 838 before it is transmitted out of host device 800.

Plus, host device 800 may further be configured to make an entry in the memory, if it is detected that the electrode does not contact fully the skin of the patient. The entry can be of the date, time, other available data including patient data, and efforts to emit the alert.

Moreover, host device 800 may include another module 825. Other module 825 can be configured to measure a physiological parameter of the patient, which can be other than the patient's ECG. In some embodiments, the local parameter is a trend that can be detected in a monitored physiological parameter of the patient. A trend can be detected by comparing values of parameters at different times.

Additionally, host device 800 may include a defibrillator 888. Defibrillator 888 can be configured to transmit an electrical defibrillation pulse through electrode port 811, in the event that electrode 810 is a defibrillation electrode.

As described above, the alert can be auditory, visual or tactile. In some embodiments, the alert identifies the electrode that is coming off the skin, thus distinguishing it from another electrode. The alert could include a picture of the electrode in question. The picture could also be in a context, such as indicating the location of the electrode.

Host device 800 may also emit the alert electronically to a remote care giver, as a transmitted message. The message may be transmitted over a communication network wirelessly or not.

In some embodiments, host device 800 is part of a wearable defibrillation system. Embodiments are now described in more detail, also with reference to FIG. 9.

A wearable defibrillator system made according to embodiments has a number of components. One of these components is a support structure, which is configured to be worn by the patient. The support structure can be any structure suitable for wearing, such as a harness, a vest, one or more belts, another garment, and so on. The support structure can be implemented in a single component, or multiple components. For example, a support structure may have a top component resting on the shoulders, for ensuring that the defibrillation electrodes will be in the right place for defibrillating, and a bottom component resting on the hips, for carrying the bulk of the weight of the defibrillator. A single component embodiment could be with a belt around at least the torso. Other embodiments could use an adhesive structure or another way for attaching to the person, without encircling any part of the body. There can be other examples.

Figure 9:
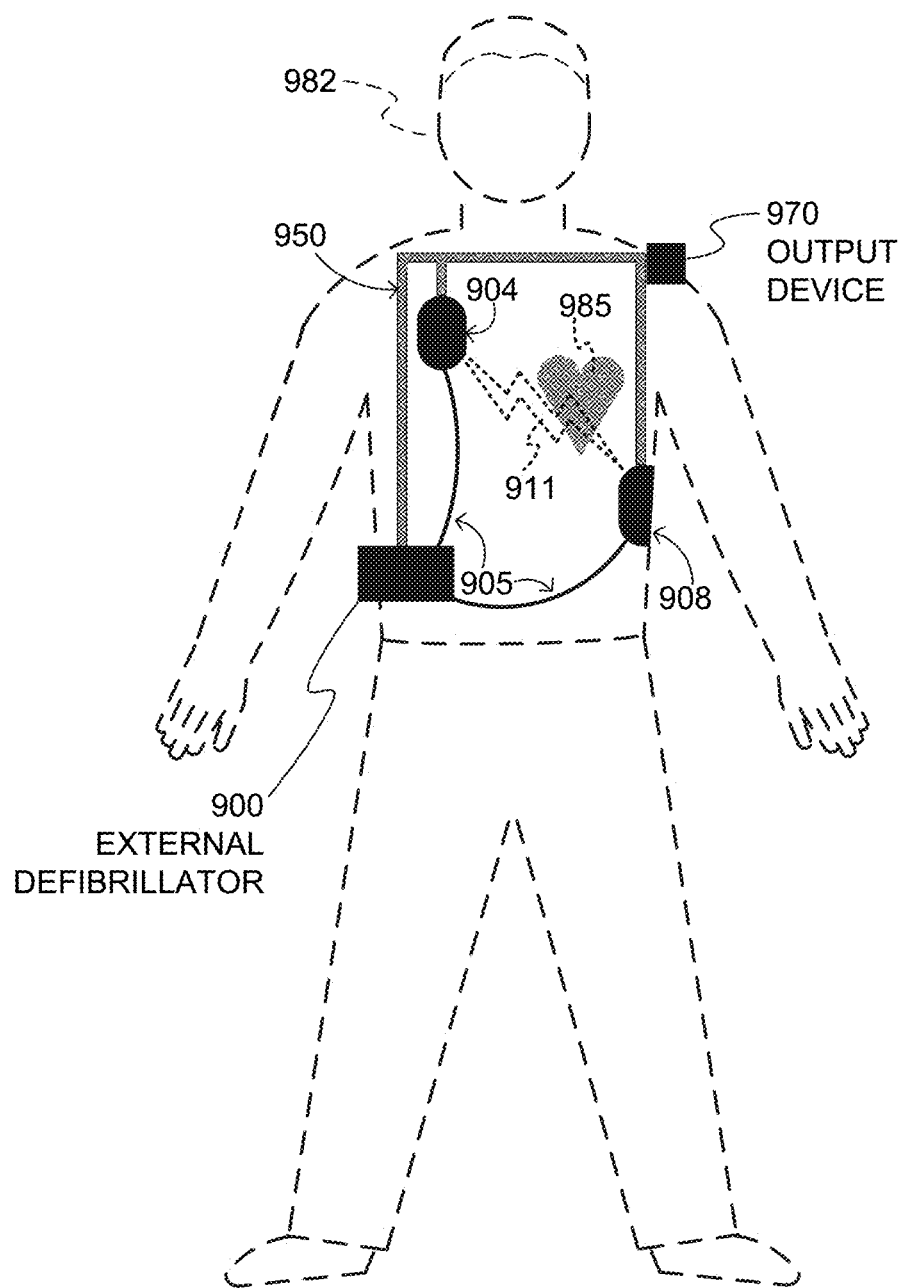
FIG. 9 is a diagram of components of a wearable defibrillator system made according to embodiments.

FIG. 9 is a diagram of components of a wearable defibrillator system made according to embodiments, as it might be worn by a patient 982. Patient 982 may also be referred to as person 982, and/or wearer 982 since he or she wears components of the wearable defibrillator system.

In FIG. 9, a generic support structure 950 is shown relative to the body of person 982, and thus also relative to his or her heart 985. Structure 950 could be a harness, a vest, one or more belts, a garment, as per the above; it could be implemented in a single component, or multiple components, and so on. Structure 950 is wearable by person 982, but the manner of wearing it is not depicted, as structure 950 is depicted only generically in FIG. 9.

A wearable defibrillator system is configured to defibrillate the patient, by delivering electrical charge to the patient's body in the form of an electric shock or one or more pulses. FIG. 9 shows a sample external defibrillator 900, and sample defibrillation electrode pads 904, 908, which are coupled to external defibrillator 900 via electrode leads 905. Defibrillator 900 can be made as device 300 of FIG. 3, or in other ways. Defibrillator 900 is coupled to support structure 950. As such, all components of defibrillator 900 can be therefore coupled to support structure 950. When defibrillation electrode pads 104, 108 make good electrical contact with the body of person 982, defibrillator 900 can administer a brief, strong electric pulse 911 through the body, similar to pulse 111 of FIG. 1.

A wearable defibrillator system according to embodiments includes an output device 970. In some embodiments, output device 970 is coupled to support structure 950. In some of these embodiments, output device 970 is coupled such that it is positioned near the patient's shoulder. This way, an alert that is intended for wearer 982 can be heard more reliably, if it is audible.

It should be remembered that a wearable defibrillator system according to embodiments may include electrodes that can have another output device on the pad, or the output device only on the pad. This way a tactile alert will be perceived at the location of the worn electrode.

The above-mentioned devices and/or systems perform functions, processes and/or methods, as described in this document. The functions, processes and/or methods may be implemented by one or more devices that include logic circuitry. The logic circuitry may include a processor that may be programmable for a general purpose, or dedicated, such as processor 830.

Moreover, methods and algorithms are described below. These methods and algorithms are not necessarily inherently associated with any particular logic device or other apparatus. Rather, they are advantageously implemented by programs for use by a computing machine, such as a general-purpose computer, a special purpose computer, a microprocessor, etc.

Often, for the sake of convenience only, it is preferred to implement and describe a program as various interconnected distinct software modules or features, individually and collectively also known as software. This is not necessary, however, and there may be cases where modules are equivalently aggregated into a single program, even with unclear boundaries. In some instances, software is combined with hardware, in a mix called firmware.

This detailed description includes flowcharts, display images, algorithms, and symbolic representations of program operations within at least one computer readable medium. An economy is achieved in that a single set of flowcharts is used to describe both programs, and also methods. So, while flowcharts described methods in terms of boxes, they also concurrently describe programs.

A method is now described.

Figure 10:
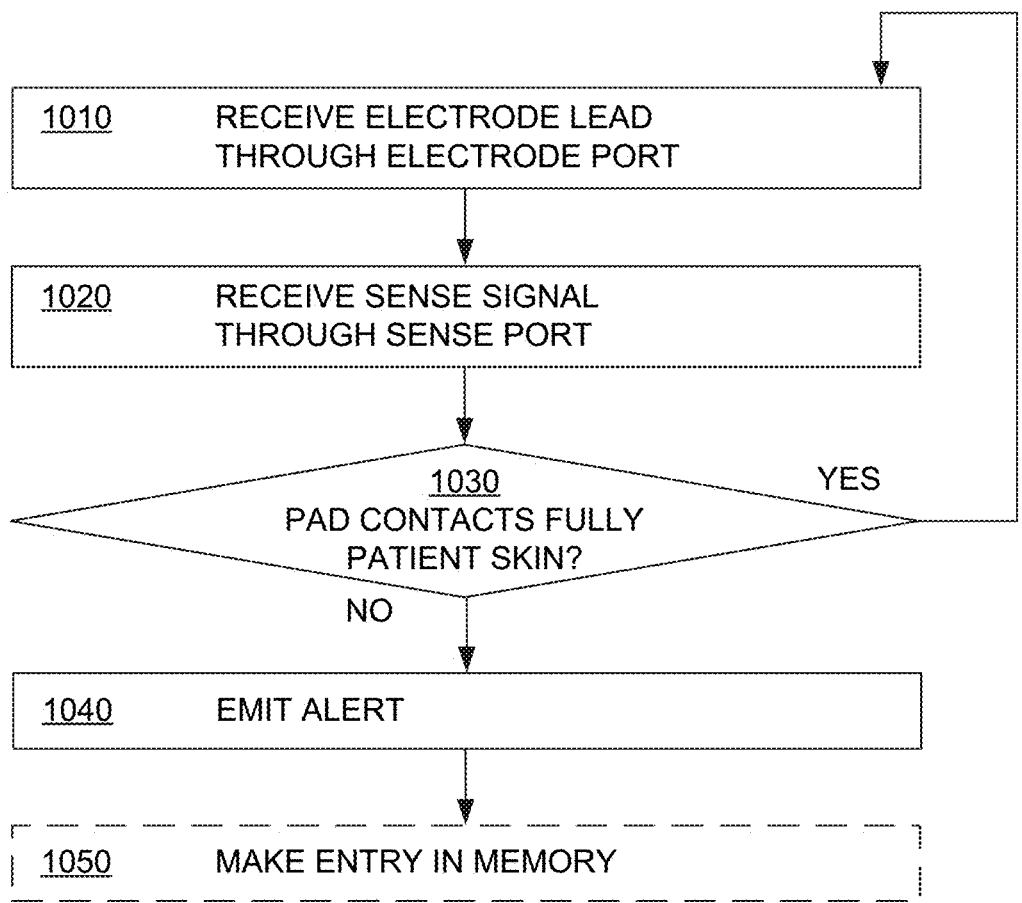
FIG. 10 is a flowchart for illustrating methods according to embodiments.

FIG. 10 shows a flowchart 1000 for describing methods according to embodiments. The methods of flowchart 1000 may also be practiced by embodiments described above, such as host device 800.

According to an operation 1010, an electrode lead is received through the electrode port. The electrode lead is of an electrode having a pad for contacting a patient's skin, and a contact detector.

According to another operation 1020, a sense signal is received through the sense port. The sense signal is received from the contact detector, either via sense leads or wirelessly.

According to another operation 1030, it is determined whether the pad contacts fully the skin of the patient. The determination may be from the received sense signal, which informs of the state of the contact detector. In some embodiments, the sense signal is null unless operation 1030 results in "no". In some embodiments, the sense signal is nonzero. Depending on the design, there can be an affirmative operation of determining from the sense signal whether the electrode does not contact fully the skin of the patient. If the determination of operation 1030 results in "yes", execution returns to operation 1010.

If the determination of operation 1030 results in "no", then according to another operation 1040, an alert is emitted by the output device. In some embodiments, the alert signal is null unless operation 1030 results in "no". Then the output device only operates based on the sense signal being nonzero. The alert may be emitted as mentioned above.

According to another, optional operation 1050, an entry is made in a memory. The entry can be made if it is detected that the electrode does not contact fully the skin of the patient.

There can be further other optional operations. For example, an ECG of the patient can be measured through the electrode port. Or a physiological parameter of the patient, other than the patient's ECG, can be measured. Or, an electrical defibrillation pulse can be transmitted through the electrode port.

Moreover, the output device may be used also for other notifications. For example, another condition of the patient may be detected, such as from measuring their physiological parameters. The condition may be that a parameter is trending in a way that causes concern, and so on. When the other condition is detected, the output device may emit an alert.

The invention also includes methods for processor 830. Processor 830 receives inputs and causes devices, modules and components to execute functions. Some of the resulting methods are those of FIG. 10.

In some embodiments, a processor may decode a sense signal. The sense signal may have been received through the sense port. The sense signal may be from a contact detector of an electrode that has a pad for contacting a patient's skin. Then it may be determined from the sense signal whether the pad does not contact fully the skin of the patient and, if so, the output device can be caused to emit an alert. The alerts can be as above.

RFID-Based Sensing

Figure 11:
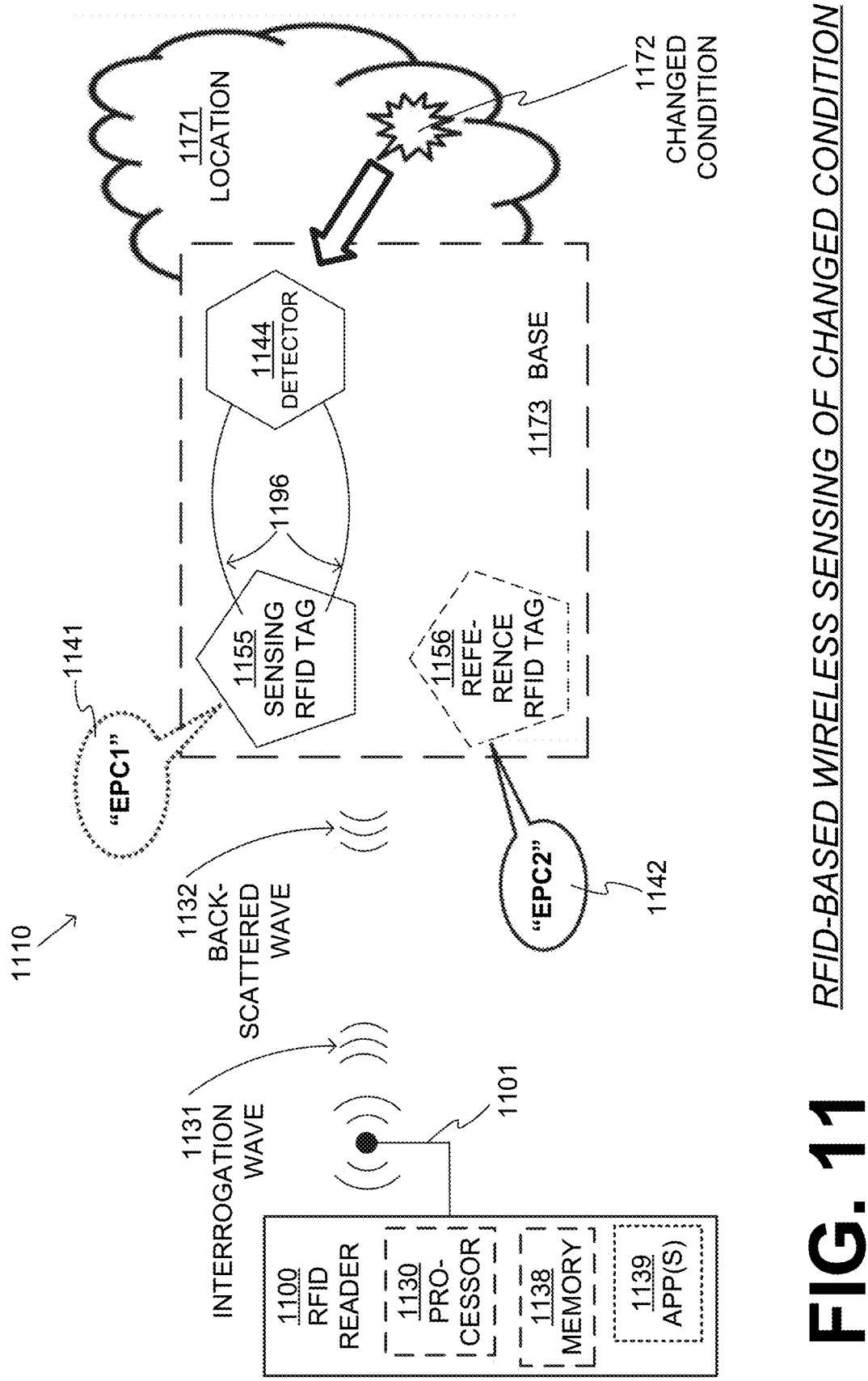
FIG. 11 is a diagram illustrating RFID-based wireless sensing of a changed condition, according to embodiments.

FIG. 11 is a diagram illustrating RFID-based wireless sensing of a changed condition, according to embodiments. It will be appreciated that the sensing can be in any number of frequencies, such as 13.56 MHz, 900 MHz, 2.4 GHz and so on. Moreover, where two RFID tags are shown, it is preferred and advantageous that they work in the same frequency, but that is not necessary.

A changed condition 1172 is shown in FIG. 11 at a location 1171. The condition that could change is illumination, temperature, available mass, capacitance, sound, pressure, humidity, and so on, and the desire is to have a system that detects it without the need for inspection, for example whether a basement leaks water, electrodes losing full contact, etc. A person skilled in the art will find many more uses.

Embodiments include an RFID-based sensor 1110. Sensor 1110 includes a base 1173 that is optional and highly preferred. One or all the other components of sensor 1110 can be coupled to base 1173. Base 1173 can be made in any way suitable for the described functions such as, for example, from plastic that is hard or flexible.

If the change of condition needs to be detected at a specific location such as location 1172, then base 1173 could be configured to be placed at that location. For example, base 1173 may further have provisions for its attachment, such as a clear flap suitable for gluing or nailing to a place of interest. It is also recommended that base 1173 have a clear area to accommodate writing, for better identification of the sensors at their locations.

Sensor 1110 also includes a sensing RFID tag 1155. Sensing RFID tag 1155 may be coupled to base 1173, if provided. The word "sensing" in the name of sensing RFID tag 1155 is only for distinguishing from the other RFID tag, if provided. Advantageously, sensing RFID tag 1155 can be procured from commercially available RFID tags.

Sensor 1110 additionally includes a detector 1144. Detector 1144 has an electrical property that may change responsive to a change in the condition, which is why an arrow is shown from changed condition 1172 to detector 1144. The detector can be of the technology applicable for the condition to be detected. As such, the detector can be a light detector, a temperature sensor, a capacitance sensor, a sound detector, a pressure sensor such as piezoelectric technology, a humidity detector, and so on. Depending on the operation of the detector, the electrical property that changes when the condition changes can be a generated voltage, a generated current, a changed impedance, and so on.

In addition, detector 1144 is electrically coupled to sensing RFID tag 1155. Coupling can be by manufacturing detector 1144 suitably close to the RFID tag. Alternately, detector 1144 can be electrically coupled via jumper wires 1196. If used, jumper wires 1196 are preferably kept short. Changed condition 1172 will generate a change in the electrical property of detector 1144, which in turn will impact an operation of sensing RFID tag 1155. The change in operation can be detected by an interrogating RFID reader, which will thus know about the changed condition 1172.

Sensor 1110 optionally also includes a reference RFID tag 1156. Reference RFID tag 1156 may be coupled to base 1173, if provided. Again, reference RFID tag 1156 can be procured from commercially available RFID tags. If reference RFID tag 1156 will be used for dynamically writing to it periodic information such as received signal strength, then it should be the type that can be written.

Reference RFID tag 1156 is not electrically coupled to detector 1144 as is sensing RFID tag 1155. This means that reference RFID tag 1156 is coupled to detector differently than sensing RFID tag 1155, or not at all. As such, while the changed condition will impact the operation of sensing RFID tag 1155, it will not impact that of reference RFID tag 1156.

In fact, it should be considered that in location 1171, if there is a changed condition 1172, the operation of both tags may be affected. That is why, in some embodiments, sensor 1110 also includes a shield that is configured to shield reference RFID tag 1156 differently than sensing RFID tag 1155, so that the latter will not be impacted by changed condition 1172. Shielding differently means that sensing RFID tag 1155 may be shielded in part, or not at all, by the shield.

More can be done by exploiting the Electronic Product Codes (EPCs) that can be stored in the memories of RFID tags 1155, 1156. For example, sensing RFID tag 1155 can have a first memory that stores a first EPC ("EPC1"), and reference RFID tag 1156 can have a second memory that stores a second EPC ("EPC2"). EPC2 can be related to EPC1, so that an RFID reader will know the relationship of the two RFID tags, and it will be easier to select them for interrogation while quieting any other tags in location 1171. In fact, the first EPC could include a string in common with the second EPC.

Embodiments include an RFID reader 1100, which can be configured to sense the impacted operation of sensing RFID tag 1155. RFID reader 1100 may have an antenna 1101, a processor 1130, and a memory 1138 that could store reader software applications ("apps") 1139 according to embodiments. Antenna 1101 can transmit and receive waves at the desired frequency for the RFID application. In some embodiments, a different antenna transmits, while antenna 1101 receives. A Received Signal Strength Indicator (RSSI) module may also be provided with reader 1100, which is configured to measure a strength of the backscattered signal.

RFID reader 1100 may transmit an interrogation wave 1131 towards location 1171, where sensor 1110 is at. Antenna 1101 may receive a backscattered wave 1132 in response to the transmitted wave. Backscattered wave 1132 will include response 1141 from sensing RFID tag 1155, and response 1142 from reference RFID tag 1156, if provided. As can be seen from FIG. 11, response 1141 can be code EPC1, and response 1142 can be code EPC2. Moreover, if reader 1100 follows a protocol that singulates the RFID tags, it will be able to discern code EPC1 from code EPC2. However, response 1141 may be received at a different strength, also known as signal strength, if changed condition 1172 has caused detector 1144 to impact the operation of sensing RFID tag 1155. And, as will be seen in embodiments, response 1141 might be too weak to be received, or it might not be received at all, and that is why it is drawn as a "whisper".

Accordingly, from the strength of backscattered wave 1132, processor 1130 may be able to determine that condition 1172 has changed. Processor 1130 may be further configured to transmit an alert to an operator or a monitoring service, if condition 1172 has changed.

The determination can be made in a number of ways. In one embodiment, the determination can be made by comparing the strength of response 1141 to a strength of a previously received backscatter from the location. A value of that strength may have been stored in memory 1138 for future comparison. If the strength of the presently backscattered wave has become less, then the condition may be changing.

In an additional embodiment, the determination is made if the strength of the backscattered wave is lower than a threshold. The threshold can be set appropriately. This type of embodiment also takes care of the possibility that backscattered wave 1132 reaching antenna 1101 is too weak to be measured, or that response 1141 is not generated at all.

In another embodiment, the backscattered wave includes a stored value of a previously measured signal strength from the location. In other words, once that signal strength was measured previously, its value stored back in the memory of sensing RFID tag 1155, for future comparison. The determination can then be made by comparing the strength of the presently backscattered wave to the stored value. Also, memory 1138 can be configured to store the value of present response 1141, for future comparison.

In one more embodiment, the determination is made by effectively comparing the signal strength of response 1141, which is presumed to be backscattered by sensing RFID tag 1155, to that of response 1142, which is presumed to be backscattered by reference tag 1156. In an ideal situation, when there is no changed condition, the signal strengths of responses 1141 and 1142 could be identical. Due to jumper wires 1196, however, they might not be. Still, their ratio can provide good guidance—if it deteriorates in the future, that could mean there is changed condition 1172. So, the determination can be made by comparing a detected ratio of the strength of the first response to that of the second response, against that of a previously detected ratio. Plus, performance values of sensing RFID tag 1155 can be stored in the memory of the reference tag 1156 that is less prone to loss due to changed condition 1172. The strength of this technique is that changes in other conditions are not automatically misinterpreted as changed condition 1172, because the backscatter signal strength of the reference tag 1156 will also be affected. An example of another such condition is if reader 1100 subsequently transmits at lesser power.

As has been mentioned, sensor 1110 is specially made such that the change in the electrical property of detector 1144 will impact the performance of sensing RFID tag 1155. Moreover, it is very economical to achieve this by procuring a commercially available RFID tag as sensing RFID tag 1155, and generally electrically coupling it to detector 1144 via jumper wires 1196. Particular examples of such coupling are now described with reference to FIGS. 12 and 13.

FIG. 12 is a diagram illustrating electrical connections for an RFID-based sensor according to embodiments. Sensing RFID tag 1255 has a substrate 1291 and a sensing antenna 1292 on substrate 1291. The term "sensing" in the name of sensing antenna 1292 is only to distinguish from the antenna of any other RFID tag, if provided. The sensing antenna can be any shape. The specific shape of sensing antenna 1292 in the example of FIG. 12 is from U.S Design Pat. D543,9765 to Impinj for the 900 MHz range, and chosen here so that the simplicity of its pattern would not unnecessarily confuse the description, but many other antenna designs may work just as well, or even better.

Sensing RFID tag 1255 also has a tag chip 1293 on substrate 1291. Tag chip 1293 is a rectangle that is much smaller than sensing antenna 1292, and has conductive pads at its corners. Antenna 1292, as well as many other antennas, terminates in four edges that are contacted by the conductive pads of tag chip 1293.

A detector 1244 is electrically coupled to sensing antenna 1292, by jumper wires 1296 that are electrically connected at nodes 1297. Coupling can be by soldering. If antenna 1292 is covered by a plastic cover, that cover may have to be removed first at the location of nodes 1297.

The connections of FIG. 12 can be used so that the performance of sensing RFID tag 1255 will be impacted mainly by detuning the sensing antenna. Indeed, when the electrical property of detector 1244 changes because of the changed condition, the impact on sensing antenna 1292 will be felt from nodes 1297, which are "in the middle" of sensing antenna 1292, and "far" from where it contacts tag chip 1293. The antenna properties will likely change, and thus its reflectivity will change.

If a commercially available RFID tag 1255 has been used that was already tuned to optimum reflectivity, then the changing property of detector 1244 will detune it and diminish the reflectivity. That is why response 1141 may be weak.

Not all detectors work the same way. In general, a meshing circuit 1245 can be coupled between detector 1244 and sensing antenna 1292. In the example of FIG. 12, meshing circuit 1245 is coupled in parallel.

Meshing circuit 1245 can be designed so that the particular changing property of detector 1244 becomes an important effect that impacts the operation of tag chip 1255, and in this case its reflectivity. For example, meshing circuit 1245 could have a resistor, a capacitor, both, etc. If detector 1244 changes impedance due to the changed condition, then meshing circuit 1245 can provide impedance of a suitable value that is added in parallel.

The connections of FIG. 12 can be also used to disrupt the tag chip operation. For example, if detector 1244 generates current due to the changed condition, then meshing circuit 1245 can be a high resistance resistor that creates a DC voltage, some of which can be applied to tag chip 1293.

FIG. 13 is a diagram illustrating electrical connections for an RFID-based sensor according to embodiments. Sensing RFID tag 1355 has a substrate 1391 and a sensing antenna 1392 on substrate 1391. Sensing antenna 1392 is the same as antenna 1292, to further illustrate the difference. Sensing RFID tag 1355 also has a tag chip 1393 on substrate 1391.

A detector 1344 is electrically coupled to sensing antenna 1392, by jumper wires 1396 that are electrically connected at nodes 1397. Coupling can be by soldering.

A meshing circuit 1345 can be coupled between detector 1344 and sensing antenna 1392. In the example of FIG. 13, meshing circuit 1345 is coupled in series.

The connections of FIG. 13 are intended so that the performance of sensing RFID tag 1355 will be impacted mainly by disrupting the operation of tag chip 1393. Indeed, when the electrical property of detector 1344 changes because of the changed condition, the impact will be felt from nodes 1397, which are near tag chip 1393. For example, if detector 1344 generates current due to the changed condition, then meshing circuit 1345 can be a high resistance resistor that creates a DC voltage, some of which can be applied to tag chip 1393. Depending on the design of tag chip 1393, the DC voltage may impact the operation of the demodulator and/or the modulator of tag chip 1393, perhaps preventing it from sensing properly the reader signal, or responding properly. This will be achieved more easily if an antenna design is chosen, and nodes are chosen that are not shorted to each other by the antenna itself.

An advantage is that, while it was intended to impact tag chip 1393, this was accomplished without having to solder to its pads, but by choosing nodes 1397 near it. Reasons to use a commercially available RFID tag are both that it is cheap, and that the low cost already incorporates the made connection between antenna 1392 and tag chip 1393 that requires high precision to make.

Other options include making custom antenna designs for such chips, and designing the detector in the tag chip, especially if the latter can be implemented in CMOS.

Figure 14:
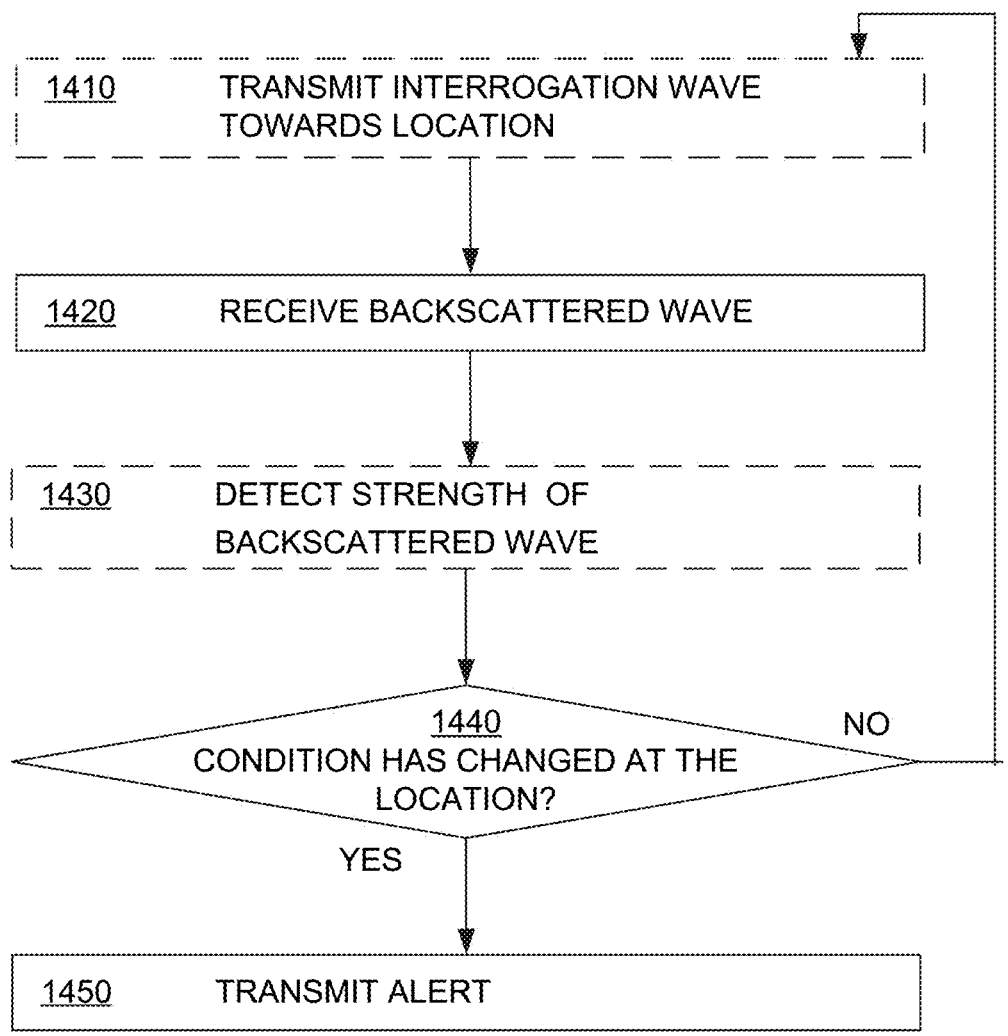
FIG. 14 is a flowchart for illustrating methods according to embodiments.

FIG. 14 shows a flowchart 1400 for describing methods according to embodiments. The methods of flowchart 1400 may also be practiced by embodiments described above, such as by reader 1100 or one of its components, for example by reader software.

According to an optional operation 1410, an interrogation wave is transmitted towards the location of interest. Preferably, a sensor such as sensor 1110 has been placed there, and which has one or more RFID tags.

According to another operation 1420, a backscattered wave is received. The backscattered wave may be received in response to the interrogation wave. The backscattered wave may have encoded information that identifies the sensor that is responding this way.

According to another, optional operation 1430, the strength of the received backscattered wave is detected. The detected strength may also be recorded, both locally in the reader and also in an RFID tag on the responding sensor.

According to another operation 1440, it is determined whether a condition has changed at the location. The determination can be made from the strength of the backscattered wave, and also as described above. If not, then execution may return to operation 1410.

If yes, then according to another operation 1450, an alert is transmitted. The alert can be transmitted by proper messaging to a different module in the host or a different device.

In the methods described above, each operation can be performed as an affirmative step of doing, or causing to happen, what is written that can take place. Such doing or causing to happen can be by the whole system or device, or just one or more components of it. In addition, the order of operations is not constrained to what is shown, and different orders may be possible according to different embodiments. Moreover, in certain embodiments, new operations may be added, or individual operations may be modified or deleted. The added operations can be, for example, from what is mentioned while primarily describing a different system, device or method.

This description includes one or more examples, but that does not limit how the invention may be practiced. Indeed, examples or embodiments of the invention may be practiced according to what is described, or yet differently, and also in conjunction with other present or future technologies.

A person skilled in the art will be able to practice the present invention in view of this description, which is to be taken as a whole. Details have been included to provide a thorough understanding. In other instances, well-known aspects have not been described, in order to not obscure unnecessarily the present invention.

Other embodiments include combinations and sub-combinations of features described herein, including for example, embodiments that are equivalent to: providing or applying a feature in a different order than in a described embodiment; extracting an individual feature from one embodiment and inserting such feature into another embodiment; removing one or more features from an embodiment; or both removing a feature from an embodiment and adding a feature extracted from another embodiment, while providing the advantages of the features incorporated in such combinations and sub-combinations.

The following claims define certain combinations and subcombinations of elements, features and steps or operations, which are regarded as novel and non-obvious. Additional claims for other such combinations and subcombinations may be presented in this or a related document.

What is claimed is:

1. A method for a patient electrode having a pad adapted to be attached onto a skin of a patient, a contact detector coupled to the pad and adapted to be in one of a plurality of detector states, and an output device, the method comprising:
   determining from a current one of the detector states whether the pad has adversely affected contact with the skin of the patient, the patient electrode further having an electrode lead coupled to the pad; and
   providing, by the output device, an alert responsive to determining from the current one of the detector states that the pad has adversely affected contact with the skin of the patient, the output device coupled to one of the pad and the electrode lead;
   wherein a sense signal is generated that encodes the current one of the detector states, wherein the sense signal comprises a Radio Frequency Identification (RFID) interrogation wave transmitted to an RIFD tag of the patient electrode, and
   wherein the output device provides the alert responsive to receiving a version of the sense signal when the version of the sense signal indicates the pad has adversely affected contact with the skin of the patient.

2. The method of claim 1, in which the detector states are different values of an electrical property of the contact detector.

3. The method of claim 1, in which the contact detector comprises a capacitive sensor, the plurality of detector states indicate a detected capacitance from a mass of the patient, and determining from the current one of the detector states that the pad has adversely affected contact with the skin of the patient is performed responsive to the detected capacitance changing beyond a threshold.

4. The method of claim 1, further comprising:
   querying the contact detector about the current detector state, and
   in which the determining is performed responsive to the querying.

5. The method of claim 1, further comprising:
   querying the contact detector about the current detector state, and
   the sense signal is generated responsive to the querying.

6. The method of claim 1, in which
   the patient electrode further has a sense lead, and
   the sense signal is transferred by the sense lead.

7. The method of claim 1, in which
   the sense signal is wireless.

8. The method of claim 7, in which
   the patient electrode further comprises the Radio Frequency Identification (RFID) tag coupled to the contact detector, the RFID tag is adapted to be interrogated by an RFID reader, and the RFID tag backscatters the sense signal responsive to being interrogated.

9. A method for a combination of a patient electrode and an output device, the patient electrode having a pad adapted to be attached onto a skin of a patient, an electrode lead coupled to the pad, and a contact detector that is configured to be in one of a plurality of detector states, a current one of the detector states determinative that the pad has adversely affected contact with the skin of the patient, the method comprising:

generating a wireless sense signal that encodes the current detector state, wherein the wireless sense signal comprises a Radio Frequency Identification (RFID) interrogation wave transmitted to an RIFD tag of the patient electrode; and the output device providing an alert responsive to receiving a version of the sense signal when the version of the sense signal indicates the pad has adversely affected contact with the skin of the patient.

10. The method of claim 9, in which
the detector states are different values of an electrical property of the contact detector.

11. The method of claim 9, in which
the contact detector comprises a capacitive sensor, the plurality of detector states indicate a detected capacitance from a mass of the patient, and the current detector state is determinative that the pad has adversely affected contact with the skin of the patient responsive to the detected capacitance having a value beyond a threshold.

12. The method of claim 9, further comprising:
querying the contact detector about the current detector state, and in which the sense signal is generated responsive to the querying.

13. The method of claim 9, in which
the patient electrode further comprises the Radio Frequency Identification (RFID) tag coupled to the contact detector, the RFID tag is adapted to be interrogated by an RFID reader, and the RFID tag backscatters the sense signal responsive to being interrogated.

14. The method of claim 1, wherein the pad is determined to have adversely affected contact with the skin of the patient when the temperature has dropped below a predetermined threshold.

15. The method of claim 1, wherein the pad is determined to have adversely affected contact with the skin of the patient when the electrode exhibits degraded properties.

* * * * *